United States Patent [19]

Reichert, Jr.

[11] 4,377,873

[45] Mar. 29, 1983

[54] INTRAOCULAR LENS

[76] Inventor: Henry L. Reichert, Jr., 810 E. Rosser Ave., Bismarck, N. Dak. 58501

[21] Appl. No.: 202,294

[22] Filed: Oct. 30, 1980

[51] Int. Cl.³ .......................... A61F 1/16; A61F 1/24
[52] U.S. Cl. ......................................................... 3/13
[58] Field of Search .......................................... 3/13, 1

[56] References Cited

U.S. PATENT DOCUMENTS

| | | | |
|---|---|---|---|
| 3,922,728 | 12/1975 | Krasnov | 3/13 |
| 3,986,214 | 10/1976 | Krasnov | 3/13 |
| 4,073,014 | 2/1978 | Poler | 3/13 |
| 4,073,015 | 2/1978 | Peyman et al. | 3/13 |
| 4,077,071 | 3/1978 | Freeman | 3/13 |
| 4,080,709 | 3/1978 | Poler | 3/13 X |
| 4,087,866 | 5/1978 | Choyce et al. | 3/13 |
| 4,092,743 | 6/1978 | Kelman | 3/13 |
| 4,126,904 | 11/1978 | Shepard | 3/13 |
| 4,134,160 | 1/1979 | Bayers | 3/13 |
| 4,139,915 | 2/1979 | Richards et al. | 3/13 |
| 4,149,279 | 4/1979 | Poler | 3/13 |
| 4,159,546 | 7/1979 | Shearing | 3/13 |
| 4,174,543 | 11/1979 | Kelman | 3/13 |
| 4,242,760 | 1/1981 | Rainin | 3/13 |
| 4,254,510 | 3/1981 | Tennant | 3/13 |
| 4,277,851 | 7/1981 | Choyce | 3/13 |

FOREIGN PATENT DOCUMENTS 1103399  5/1955  France .................................... 3/13

OTHER PUBLICATIONS

"Experience with Twelve Cases of Intra-Ocular Anterior Chamber Implants for Aphakia" by J. Boberg-Ans, British Journal of Ophthalmology, vol. 45, No. 1, Jan. 1961, pp. 37-43.
"Covered Bridge an Update on Lens Implantation" by J. H. Sheets or Bridge Over Trouble Waters (Book), 1977, pp. 5-13, Schreck Lens in FIG. 7 and Barraquer Lens in FIG. 11.

*Primary Examiner*—Ronald L. Frinks
*Attorney, Agent, or Firm*—Burd, Bartz & Gutenkauf

[57] ABSTRACT

An implantable artificial intraocular bipod lens comprising a medial light-focusing lens body having position fixation elements connected thereto. The fixation elements comprise a pair of straight elongated relatively thin and narrow legs extending tangentially in opposite directions from opposite sides of the lens body and lying along generally parallel lines. A relatively thin and narrow arcuate foot is located at the end of each of the legs. Each of the feet is longer and narrower than the width of the leg and preferably thicker than the leg. The feet extend obliquely in opposite directions. Preferably a suture/manipulation hole is provided in at least one of the legs spaced inwardly from the foot.

12 Claims, 5 Drawing Figures

U.S. Patent                Mar. 29, 1983                4,377,873
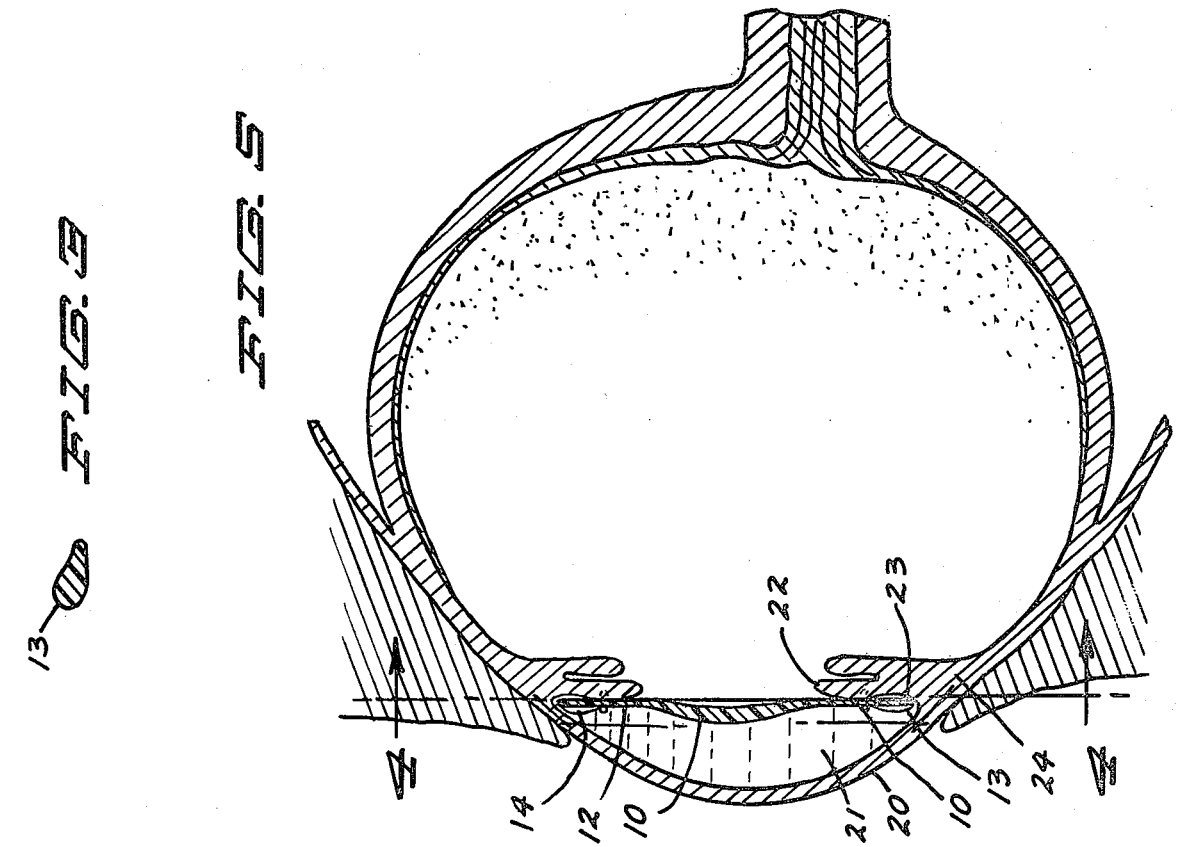
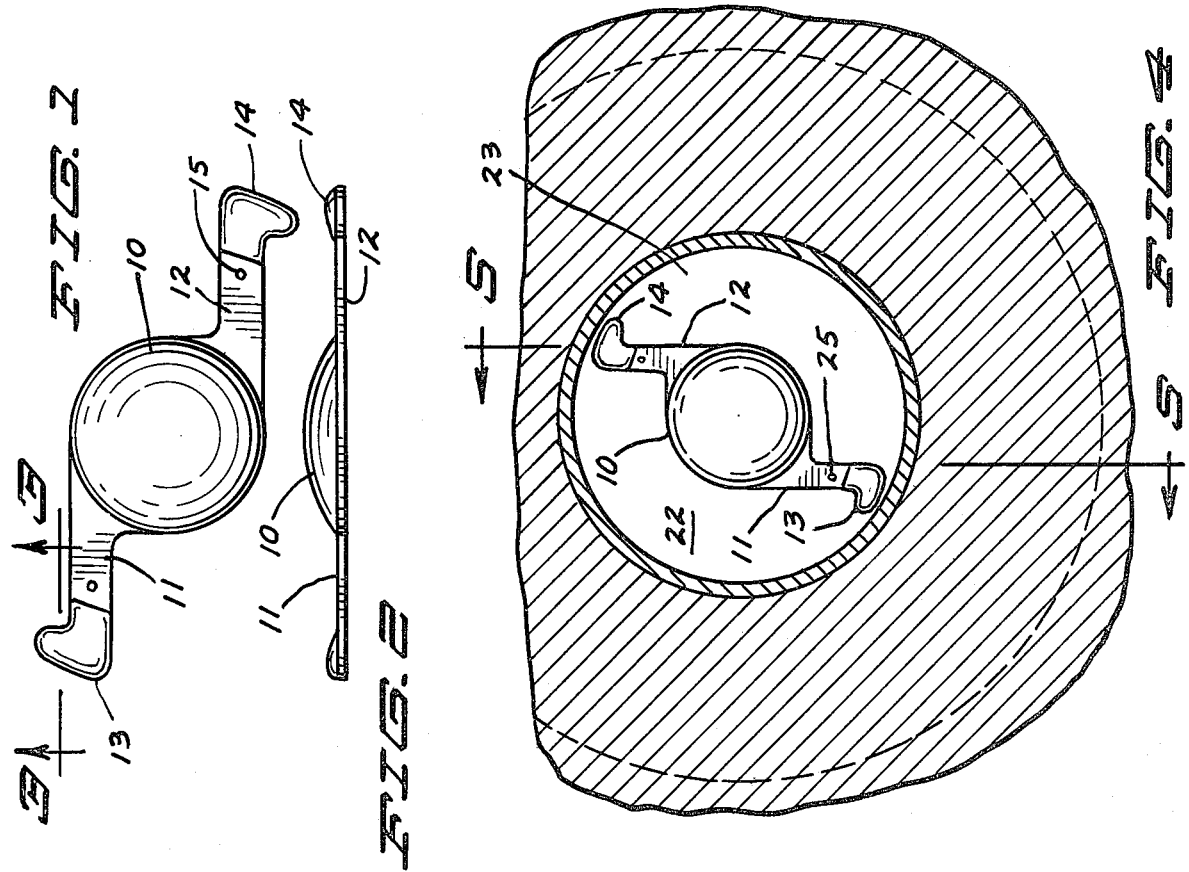

INTRAOCULAR LENS

FIELD OF THE INVENTION

1. Background of the Invention

This invention is directed to an intraocular lens for implantation in the anterior chamber of the eye following intracapsular lens extraction, extracapsular lens extraction or as a secondary implantation.

2. The Prior Art

Surgical lens implantation of artificial lenses has come into increasing use for the restoration of vision by the correction of aphakia resulting from removal of the natural lens because of a cataract condition. Many artificial lenses have been developed for this purpose. The prior art is summarized in U.S. Pat. Nos. 4,073,015 to Peyman et al, 4,087,866 to Choyce et al and 4,134,160 to Bayers. Prior art lenses have been proposed for implantation in the anterior chamber, the posterior chamber, or in the pupilary space. In anterior chamber placement, the lens is fixed, anchored or supported in the angle at the intersection of the cornea and the iris. Although the anterior chamber is the most readily accessible for such lens implantation, it is required that the lens be carefully sized and fitted to be precisely supported across the angle in order to avoid traumatizing the cornea or angle structures. The present invention is directed to an improved intraocular bipod lens for anterior chamber implantation.

SUMMARY OF THE INVENTION

Broadly stated, the implantable artificial intraocular bipod lens according to the present invention comprises a medial light-focusing lens body having position fixation elements connected thereto. The fixation elements comprise a pair of straight elongated relatively thin and narrow legs extending tangentially in opposite directions from opposite sides of the lens body and lying along generally parallel lines. A relatively thin and narrow arcuate foot is located at the end of each of the legs. Each of the feet is longer and narrower than the width of the leg and preferably thicker than the leg. The feet extend obliquely in opposite directions, away from each other and outwardly away from the lens body. Preferably a hole is provided in at least one of the legs spaced inwardly from the foot both for manipulating the lens and for suturing it to the iris.

BRIEF DESCRIPTION OF THE DRAWINGS

The invention is illustrated in the accompanying drawings in which corresponding parts are identified by the same numerals and in which:

FIG. 1 is a top plan view of the intraocular lens according to the present invention;

FIG. 2 is an elevation thereof;

FIG. 3 is a section on an enlarged scale on the line 3—3 of FIG. 1 and in the direction of the arrows;

FIG. 4 is a front elevation partly in section showing the lens implanted in an eye; and FIG. 5 is a section on the line 5—5 of FIG. 4 and in the direction of the arrows.

DETAILED DESCRIPTION OF THE PREFERRED EMBODIMENT

Referring now to the drawings, and particularly to FIGS. 1 through 3, the intraocular bipod lens comprises generally a circular convex medial light-focusing lens body 10 and a pair of similar position fixation elements in the form of legs 11 and 12 extending outwardly from the lens body. The legs 11 and 12 extend tangentially in opposite directions from opposite sides of the lens body and are generally parallel to one another. Legs 11 and 12 have relatively thin and narrow feet, 13 and 14, respectively, at the ends of each of the legs. The feet 13 and 14 extend obliquely in opposite directions, away from each other and outwardly away from the lens body 10 and terminate in distal ends which as seen in FIG. 4 are spaced from each other a distance greater than the spacing between parallel legs 11, 12. The feet are longer and narrower than the width of the legs. Preferably, as shown in FIG. 3, the feet are thicker than the legs along the outermost arcuate edge and taper inwardly.

The generally plano-convex lens body 10 preferably has a diameter of about 5.5 mm (about 4.5 to 6.5 mm) with a vault to minimize iris contact, measuring at the center about 0.5 mm (0.45 to 0.55 mm). The lens has an optical power sufficient to rectify the optical defects of the eye, i.e., between about 12 and 22 diopters of power. The overall diameter of the lens, measured between the arcuate edges of feet 13 and 14, may range from about 11.0 to 14.5 mm, varying in ½ mm steps so that the correct sized lens may be selected for proper fit for each individual patient. Each leg is about 1 mm (0.7 to 1.2 mm) wide and about 0.2 mm (0.15 to 0.25 mm) thick. Each of the feet 13 and 14 is about 2 mm (1.6 to 2.4 mm) long, about 0.5 mm (0.45 to 0.55 mm) wide, and about 0.35 mm (0.2 to 0.4 mm) thick at the outside arcuate peripheral edge.

A small hole 15 is preferably provided in at least one leg of the implant to facilitate manipulation of the lens and to allow for additional iris suture fixation, if desired. This hole is approximately 0.35 mm (0.2 to 0.5 mm) in diameter and spaced about 2 mm (1.6 to 2.4 mm) from the outer arcuate peripheral edge of the foot.

The implantable lens is formed by molding or casting and/or machining or grinding integrally in one piece from any of a number of transparent physiologically inert non-toxic biocompatible materials. Exemplary materials include methylmethacrylate resins available under the trade names Lucite and Plexiglas. A preferred material is the polymethylmethacrylate resin available under the trade name Perspex C.Q. Although made of a generally rigid material, the legs are semi-rigid since the thinness of the legs imparts some flexibility aiding greatly in fitting the lens into the eye.

Referring now to FIGS. 4 and 5, there is shown the manner in which the implantable lens is fitted into the eye. The lens is inserted through an incision in the cornea 20 into the anterior chamber 21 between the cornea and the iris 22. The lens is positioned with the feet 13 and 14 placed in such a manner as to achieve fixation in an oblique meridian about 25 degrees (about 20 to 30 degrees) from the vertical, which is the most stable considering both the vertical and horizontal line movements.

The foot pads are wedged into the scleral spur 23, the angle at the general meeting place of the cornea 20, iris 22 and sclera 24. The radius of the outer peripheral edge of each foot pad is slightly greater, i.e., the curve is slightly flatter, than that of the inner curve of the scleral spur 23 to achieve a slightly greater tension on the edges of the foot pads to minimize rotation. The greater thickness of the edges of the food pads prevents dissection of the foot pad posteriorly. Leg holes 15 facilitate manipulation of the lens. Sutures 25 in conjunction with either or both holes 15 may be used to fix the lens to the iris 22.

The oblique placement of the foot pads facilitates fixation as it is more easily observed during the time of fixation. The suggested placement is from the superior nasal quadrant, the upper quarter nearest the nose, to the inferior temporal quadrant, the lower quadrant away from the nose. This placement utilizes the natural protection afforded by the bony orbit of the eye socket.

The bipod lens design of this invention offers ease in manufacturing, increased ease in insertion, and placement of the lens, minimizing the risk of iris tuck. The simple, sophisticated design also renders insertion through a small incision easier and makes the entire lens system more lightweight. Although shown in one specific configuration, the lens may be made in the mirror image thereof.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. An implantable artificial intraocular bipod lens comprising:
   a medial generally circular light-focusing lens body,
   position fixation elements connected to and one-piece with said lens body, said fixation elements including:
   (a) a pair of generally straight and elongated relatively flat semi-rigid thin and narrow legs, said legs:
      (1) extending along substantially tangential lines in opposite directions from opposite diametric areas of the lens body, and,
      (2) extending outwardly from said lens body in spaced parallel relation,
   (b) a relatively thin and narrow flat pad-like foot at the end of and one-piece with each of said legs, each said foot:
      (1) extending in an oblique direction with respect to its connected leg,
      (2) having a length in the said oblique direction greater than the width of the associated leg, and,
      (3) extending in an opposite direction from the other said foot and away therefrom and also from said lens body, thereby to space the distal ends of the feet further from each other than the spaced relation of said legs.

2. An intraocular lens according to claim 1 wherein a hole is provided in at least one of said legs, spaced inwardly from the foot.

3. An intraocular lens according to claim 2 wherein a hole is provided in each leg.

4. An intraocular lens according to claim 1 wherein said foot is thicker than the leg.

5. An intraocular lens according to claim 1 wherein:
   (A) said lens body has a diameter of about 4.5 to 6.5 mm with a center vault of about 0.45 to 0.55 mm,
   (B) the overall diameter of the lens between the outer edges of the feet is from about 11.0 to 14.5 mm,
   (C) each of said legs is about 0.7 to 1.2 mm wide and about 0.15 to 0.25 mm thick, and
   (D) each of said feet is about 1.6 to 2.4 mm long, and about 0.45 to 0.55 mm wide.

6. An intraocular lens according to claim 4 wherein each of said feet is about 0.2 to 0.4 mm thick at its outer peripheral edge.

7. An intraocular lens according to claim 3 wherein each of said holes is about 0.2 to 0.5 mm in diameter and spaced inwardly about 1.6 to 2.4 mm from the outer peripheral edge of the foot.

8. An intraocular lens according to claim 1 wherein:
   (A) said lens body has a diameter of about 5.5 mm with a vault of about 0.5 mm,
   (B) the overall diameter of the lens between the outer edges of the feet is from about 11.0 to 14.5 mm,
   (C) each of said legs is about 1 mm wide and about 0.2 mm thick, and
   (D) each of said feet is about 2 mm long and about 0.5 mm wide.

9. An intraocular lens according to claim 4 wherein each of said feet is about 0.35 mm thick at its outer peripheral edge.

10. An intraocular lens according to claim 3 wherein each of said holes is about 0.2 to 0.5 mm in diameter and spaced inwardly from about 2 mm from the outer peripheral edge of the foot.

11. An intraocular lens according to claim 1 wherein said lens is formed from a physiologically inert, non-toxic, biocompatible synthetic resinous material.

12. An intraocular lens according to claim 11 wherein said lens is formed from polymethylmethacrylate.

* * * * *